United States Patent
Kahn et al.

(10) Patent No.: US 10,568,565 B1
(45) Date of Patent: Feb. 25, 2020

(54) UTILIZING AN AREA SENSOR FOR SLEEP ANALYSIS

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 14/469,509

(22) Filed: Aug. 26, 2014

Related U.S. Application Data

(60) Provisional application No. 61/988,208, filed on May 4, 2014.

(51) Int. Cl.
*A61B 5/00* (2006.01)
*A61B 5/11* (2006.01)

(52) U.S. Cl.
CPC .......... *A61B 5/4812* (2013.01); *A61B 5/1126* (2013.01)

(58) Field of Classification Search
CPC ............................ G05B 15/02; H05B 33/0863
USPC ............................................ 700/278; 607/88
See application file for complete search history.

(56) References Cited

U.S. PATENT DOCUMENTS

| | | |
|---|---|---|
| 3,798,889 A | 3/1974 | Chadwick |
| 4,228,806 A | 10/1980 | Lidow |
| 4,297,685 A | 10/1981 | Brainard, II |
| 4,573,804 A | 3/1986 | Kavoussi et al. |
| 5,008,865 A | 4/1991 | Shaffer et al. |
| 5,545,192 A | 8/1996 | Czeisler et al. |
| 5,928,133 A | 7/1999 | Halyak |
| 6,361,508 B1 | 3/2002 | Johnson et al. |
| 6,468,234 B1 | 10/2002 | Van der Loos et al. |
| 6,547,728 B1 | 4/2003 | Cornuejols |
| 6,928,031 B1 | 8/2005 | Kanevsky et al. |
| 6,963,271 B1 | 11/2005 | Fyffe |
| 7,106,662 B1 | 9/2006 | Acker |
| 7,280,439 B1 | 10/2007 | Shaddox |
| 7,366,572 B2 | 4/2008 | Heruth et al. |
| 2003/0095476 A1 | 5/2003 | Mollicone et al. |
| 2004/0049132 A1 | 3/2004 | Barron et al. |
| 2004/0210155 A1* | 10/2004 | Takemura ................ A61B 5/00 600/534 |
| 2005/0012622 A1 | 1/2005 | Sutton |
| 2005/0154330 A1 | 7/2005 | Loree |
| 2006/0150734 A1 | 7/2006 | Mimnagh-Kelleher et al. |

(Continued)

FOREIGN PATENT DOCUMENTS

| | | |
|---|---|---|
| DE | 19642316 A1 | 4/1998 |
| EP | 1139187 A2 | 10/2001 |

(Continued)

*Primary Examiner* — Devin B Henson
*Assistant Examiner* — Yasmeen S Warsi
(74) *Attorney, Agent, or Firm* — HIPLegal LLP; Judith Szepesi

(57) ABSTRACT

Devices, systems and methods that track various aspects of a person's sleep and environment to optimize one or more aspects of the user's environment and sleep conditions, quality and duration, together or alone, and help make the one or more users maintain and prolong his or her deep sleep status and improve the their sleep duration and quality.

19 Claims, 9 Drawing Sheets

(56) References Cited

U.S. PATENT DOCUMENTS

| | | | |
|---|---|---|---|
| 2006/0279428 A1* | 12/2006 | Sato | A61B 5/0064 340/575 |
| 2006/0293608 A1 | 12/2006 | Rothman et al. | |
| 2007/0016095 A1 | 1/2007 | Low et al. | |
| 2007/0191692 A1 | 8/2007 | Hsu et al. | |
| 2007/0287930 A1 | 12/2007 | Sutton | |
| 2008/0191885 A1 | 8/2008 | Loree, IV et al. | |
| 2009/0069644 A1 | 3/2009 | Hsu et al. | |
| 2009/0121826 A1* | 5/2009 | Song | A61B 5/11 340/3.1 |
| 2009/0177327 A1* | 7/2009 | Turner | A47C 21/003 700/275 |
| 2009/0203970 A1 | 8/2009 | Fukushima et al. | |
| 2009/0207028 A1 | 8/2009 | Kubey et al. | |
| 2010/0061596 A1* | 3/2010 | Mostafavi | A61B 5/113 382/107 |
| 2010/0152543 A1* | 6/2010 | Heneghan | G06F 19/3418 600/300 |
| 2010/0152546 A1* | 6/2010 | Behan | A61B 5/0002 600/301 |
| 2011/0015495 A1 | 1/2011 | Dothie et al. | |
| 2011/0058456 A1 | 3/2011 | De et al. | |
| 2011/0137836 A1* | 6/2011 | Kuriyama | A61B 5/1118 706/12 |
| 2011/0160619 A1 | 6/2011 | Gabara | |
| 2011/0190594 A1* | 8/2011 | Heit | A61M 21/00 600/301 |
| 2012/0232414 A1* | 9/2012 | Mollicone | A61B 5/024 600/508 |
| 2013/0012836 A1* | 1/2013 | Crespo Veiga | A61B 5/7221 600/595 |
| 2013/0053653 A1* | 2/2013 | Cuddihy | A61B 5/0205 600/301 |
| 2013/0053656 A1* | 2/2013 | Mollicone | A61B 5/0015 600/301 |
| 2013/0208576 A1* | 8/2013 | Loree, IV | G04G 11/00 368/256 |
| 2014/0005502 A1* | 1/2014 | Klap | A61B 5/113 600/301 |
| 2014/0207292 A1* | 7/2014 | Ramagem | G05B 15/02 700/278 |
| 2014/0259417 A1* | 9/2014 | Nunn | A61G 7/015 5/614 |
| 2014/0259434 A1* | 9/2014 | Nunn | A47C 27/083 5/713 |
| 2014/0276227 A1* | 9/2014 | Perez | A61B 5/4818 600/586 |
| 2014/0371635 A1* | 12/2014 | Shinar | A61B 5/6891 600/595 |
| 2015/0068069 A1* | 3/2015 | Tran | H04B 1/385 36/136 |
| 2015/0073283 A1* | 3/2015 | Van Vugt | A61B 5/113 600/476 |
| 2015/0141852 A1* | 5/2015 | Dusanter | A61B 5/6892 600/484 |
| 2015/0148871 A1* | 5/2015 | Maxik | H05B 33/0863 607/88 |
| 2015/0173671 A1* | 6/2015 | Paalasmaa | A61B 5/0022 600/301 |
| 2015/0233598 A1* | 8/2015 | Shikii et al. | F24F 11/0034 165/244 |
| 2017/0003666 A1* | 1/2017 | Nunn | G08C 17/02 |

FOREIGN PATENT DOCUMENTS

| | | | |
|---|---|---|---|
| JP | 8160172 | | 6/1996 |
| JP | 2007132581 A | * | 5/2007 |
| WO | WO9302731 | | 2/1993 |

\* cited by examiner

UTILIZING AN AREA SENSOR FOR SLEEP ANALYSIS

RELATED APPLICATION

This application claims priority to U.S. Provisional Application No. 61/988,208, filed on May 4, 2014, which is incorporated by reference in its entirety.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

During a sleep, the person's body temperature will also continue to fall throughout the night. For instance, often time a person's body temperature during the early morning (e.g., around 5:00 am) is usually one degree centigrade below his or her body temperature the evening before when they first went to sleep. Lower body temperature is believed to assist in and/or linked to deep/restorative sleep that allows the body a chance to rest and rebuild itself. As body temperature rises, deep sleep is more difficult to achieve and maintain.

BRIEF SUMMARY

The presently disclosed embodiments, as well as features and aspects thereof, are directed towards a system and method for identifying a user's sleep phase using an area motion sensor. An area motion sensor is a motion sensor that does not rely on being in contact with the user. The area motion sensor in one embodiment is one of a passive infrared (PIR), proximity sensor (using radio waves, ultraviolet, or other sensors), microwave/radar sensor, area reflective sensor, ultrasonic sensor, or video motion sensor. In one embodiment, the area motion sensor is a digital sensor, such as a passive infrared sensor (PIR sensor), which indicates motion or lack of motion.

BRIEF DESCRIPTION OF THE DRAWINGS

In the figures, like reference numerals refer to like parts throughout the various views unless otherwise indicated.

DETAILED DESCRIPTION

Figure 1A:
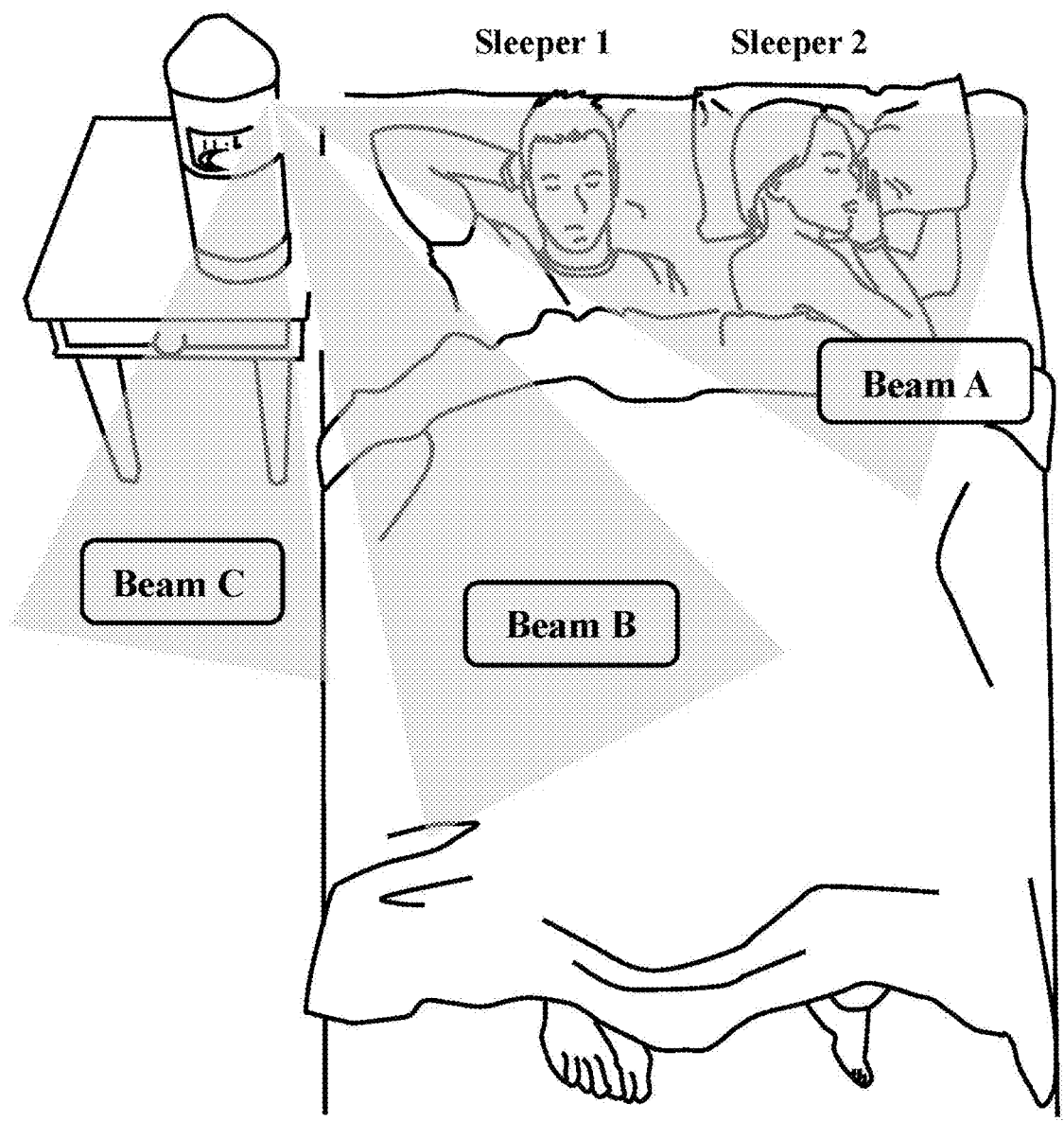
FIG. 1A is an illustration of an exemplary embodiment showing sleep tracking system with three area sensors.

The presently disclosed embodiments, as well as features and aspects thereof, are directed towards a sleep tracking system and method for detecting a user's sleep phase using an area motion sensor. The sleep tracking system may be used to improve a user's sleep environment, maximize a user's deep sleep and create a customizable environment and program for a particular user based on what works for that particular user by monitoring and analyzing the user's sleep duration, quality and stage. In one embodiment, in addition to the area motion sensor, the sleep tracking system may include other sensors, which provide further data. The sleep tracking system can be utilized to maximize a user's sleep quality, by monitoring and analyzing the user's sleep stage and adjusting the user's sleep environment.

The sleep tracking system is completely non-invasive and it requires are no awkward external components to monitor sleep. This is possible because of the area motion-sensor technology used with sensor-fusion and machine learning. The user experience is radically simplified. The sleep tracking system correlates the input from its array of sensors using advanced machine learning technology and determines the user's sleep state. This data is used to adjust the environment to help the user fall asleep faster, wake the user up at the optimal time in his or her sleep cycle so they feel more refreshed.

In one embodiment, the system may also put other aspects of the home into sleep mode, turn off lights, lock doors, adjust house temperatures, etc. In one embodiment, the system may also use the detection of the sleep state, to place a wearable device, worn by the user, into sleep mode automatically. This may be used to enable the wearable device to monitor the user's sleep, to provide more data, in one embodiment. In one embodiment, this may be used to reduce power consumption by the wearable device, when the area motion sensor is monitoring the user's sleep, and the additional data is not needed. In one embodiment, the area motion sensor may place the wearable device in sleep monitoring mode or non-monitoring mode, as needed. For example, if the sleep tracking system cannot monitor the user's sleep state using the area motion sensor, it may enable the wearable sensor to add additional data.

The sleep tracking system in one embodiment monitors and understands sleep interruptions (snore, apnea, ambulance siren, trips to the bathroom, etc.). In one embodiment, the sleep tracking device includes a smart reading light that knows when the user is falling asleep and initiates a lighting sequence that helps the user fall asleep faster when they choose to. In one embodiment, the sleep tracking system can also tap into the user's music and sound selection to create a calming and relaxed ambience for falling asleep faster. Similarly, in one embodiment, the sleep tracking system may use a waking lighting sequence and appropriate music and sounds to help the user wake up refreshed. The sleep tracking system, in one embodiment, also monitors the user's bedroom's air quality and temperature to alert the user of unhealthy conditions and monitor correlations with sleep quality. Additional local conditions may also be monitored, and adjusted when appropriate, in one embodiment.

In one embodiment, the sleep tracking system also taps into the home's Internet of Things (IoT), and can extend its reach to interface with other home controls. For example, in some embodiments, the sleep tracking system can interface with thermostats, lock doors, dim or turn on & off lights, control music, and even turn on the coffee maker in the morning.

Throughout the description, various embodiments will be referred to as an embodiment and the use of such term is not meant to be limiting but rather encompassing of all of the various embodiments, features and aspects thereof, as well as other anticipated embodiments. The word "exemplary" is used herein to mean "serving as an example, instance-, or illustration." Any aspect described herein as "exemplary" is not necessarily to be construed as exclusive, preferred or advantageous over other aspects. Though embodiments are all presented as "in one embodiment," such embodiments are not mutually exclusive or mutually inclusive, nor are features described required.

The sleep tracking system described uses an area motion sensor. An area motion sensor is a motion sensor that does not rely on being in contact with the user. Exemplary area motion sensors include passive infrared (PIR), proximity sensor (using radio waves, ultraviolet, or other sensors), microwave/radar sensor, area reflective sensor, ultrasonic sensor, video motion sensor. In one embodiment, the area motion sensor is a digital sensor, such as a passive infrared sensor (PIR sensor), which indicates motion or lack of motion only. Area sensors are generally digital, and have two states, triggered and not triggered, aka on or off. The ability to use such simple digital sensors to correctly determine the user's sleep phase would normally be considered impossible. However, the system described herein has this capability.

In one embodiment, as shown in FIG. 1A, a sleep tracking device comprises three area motion sensors A, B and C. Each area motion sensor has a range in which the sensor would be triggered, illustrated as beams A, B, and C. Each of the area motion sensors detects at least two different states (i.e., one state for movement and one state for non-movement). Three area motion sensors with two states each can provide eight different logical combinations. Furthermore, the historical data and the timing between the sensors being triggered adds additional information. Using only the data from area motion sensors, shown in FIG. 1A, the system is capable of identifying the user's sleep state. In one embodiment, the system may use the sleep state data to adjust the user's environment, to optimize for sleep quality.

In one embodiment, the sleep tracking device may include technology for passively monitoring a user to identify the migration of the user through sleep cycles. Embodiments may be implemented in a sleep tracking device that can sit on a user's night stand, hang on the wall in the user's room, attach to the user's bed post or headboard, be incorporated into a device or structure in the home or used by the user, a combination of multiple devices, or any other method or device that is known to one of one of ordinary skill in the art. In one embodiment, the sleep tracking device is designed to be plugged in, and used as a combination sleep tracking device, alarm clock, light, and/or night light. In one embodiment, the sleep tracking device may be part of a sleep tracking system which may also include a local sensor, such as an accelerometer or gyroscope to measure the user's motion more directly, other sensors and/or devices.

The area motion sensor, in some embodiments, transmits signals in the direction of the user and receives bounce backs or echoes of the signals. The transmitted signals can be ultrasonic, infrared, RF or other frequencies. When nothing is moving in the area, the bounced back signals are relatively uniform with slight variations due to temperature and air flow. However, when there is movement in the area that is being targeted, the echoed signals fluctuate. When the motion sensor detects fluctuations in the echoed signals, such as when the detected signals vary in spectrum, it is an indication that movement is occurring (i.e., the user is moving in bed).

In one embodiment, the area motion sensor is a passive infrared sensor (PIR sensor). In one embodiment, differential detection is used with the PIR sensor. Differential detection uses a paired set of sensor elements, such that the measurements cancel each other, to remove the average temperature in the field of view from the signal. This allows the sensor to avoid false indications of charge, and minimizes common-mode interference.

Figure 1B:
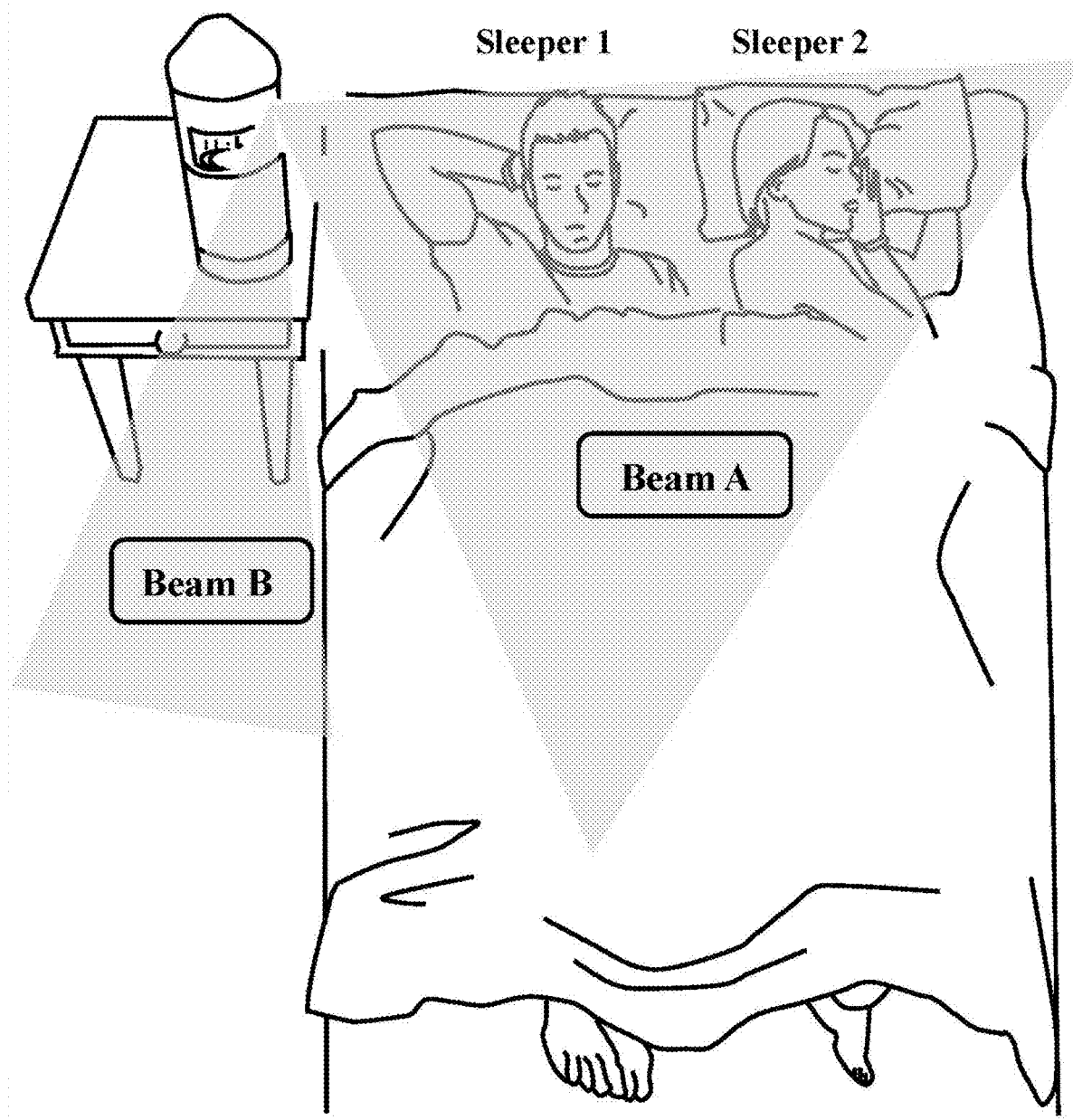
FIG. 1B is an illustration of an exemplary embodiment showing sleep tracking system with two area sensors.

In one embodiment, a sleep tracking device containing at least two area motion sensors detects the user's sleep state. FIG. 1B shows a sleep tracking device including two area motion sensors, one covering the bed area, and one covering the area next to the bed.

In one embodiment, the sleep tracking device may include additional sensors. The device may include, or receive data from sensors which can detect, in one embodiment, one or more of user movement, movement of other objects in the user's room, light levels, room temperature, air quality, oxygen level, carbon dioxide or other gas or particulate levels, user sleep state, humidity, sound, one or more user's body temperature, sleep cycles, and/or any data a sensor now known or developed in the future can detect. In one embodiment, based on the data from sensor(s), the sleep tracking system identifies the sleep state of the user(s) and determines the action or actions to be taken to adjust the sleeping environment of the user(s) to optimize the environment, help maintain and prolong the user's deep sleep status, improve the user's sleep duration and quality, and wake the user refreshed.

In one embodiment, various parameters the user's sleep environment are adjusted gradually and the effect on the user and the user's sleep cycle, quality, and duration is monitored. In one embodiment, the various parameters of two users' sleep environment is adjusted and monitored to determine the optimal environment for multiple users, sharing the same bed or sleeping environment. In some of the embodiments, the sleep tracking system monitors the effects and outcome of changing the environment, and based on the effect the adjustments have on the user's sleep duration and quality, the sleep tracking system determines whether additional aspects of the one or more user's environment should be changed to provide an optimal environment and, through various changes in the user's environment and feedback on how those changes effected the user's sleep cycles, duration and quality, determines the optimal conditions for a user, more than one user or two or more users in the same environment or bed. In one embodiment, in addition to automatic feedback, the user may provide his or her personal feedback to the system as well.

The sleep tracking system includes a sleep tracking device using an area motion sensor system for monitoring a user, to identify sleep cycles of the user. The sleep tracking device may be a device that can sit on a user's night stand, hang on the wall in the user's room, attach to the user's bed post or headboard, etc. By using an area motion sensor, rather than an accelerometer, no interaction with the user is required to activate or control the system. There is nothing that requires charging, plugging in, downloading, etc. There is nothing to lose, or misplace. Rather, the sleep tracking device can simply sit on the user's night stand, or elsewhere in the sleeping area, and monitor the user(s). Additionally, the sensor is lower cost, and more reliable.

In one embodiment, as shown in FIG. 1A, the sleep tracking device with multiple sensors can be used for multiple users in the same bed or area. The sleep tracking device uses the multiple non-overlapping sensor areas, shown as Beams A, B, and C, to determine the motions of each user, and calculate the sleep data for each user based on that information. In one embodiment, the users may have different preferences, and the system may be able to adjust preferences, such as temperature, sleep surface softness, sound and light levels, for each of the users.

In one embodiment, the sleep tracking system may include a plurality of sleep tracking devices. In one embodiment, this enables multiple users to have a separate sleep tracking devices. When multiple sleep tracking devices interact with each other, in one embodiment, they create a schedule and an environment that is most suitable for all of the users. For example, User A and User B each have a sleep tracking device. When A and B are in the same room or sharing the same bed, User A's sleep tracking device will interact with User B's sleep tracking device to create an optimal schedule and environment for both users. In one embodiment, if User A needs to wake up before User B, the sleep tracking device will initiate a more gentle method (e.g., low level music, vibration, soft light) to wake User A so that User B will not be disturbed. If User A and User B enjoy different temperature and darkness, the sleep tracking device may further adjust the mattress to different temperatures and adjust lighting to have different levels of darkness in different areas. In one embodiment, when multiple sleep tracking devices are working together in a sleep tracking system, there are more sensors, and the accuracy of the system will increase. In one embodiment, the multiple sleep tracking devices can communicate with each other to determine the best parameters for the two people sleeping in the same environment, where the chosen parameters will be a combination/variation of the ideal parameters for each user.

Figure 2A:
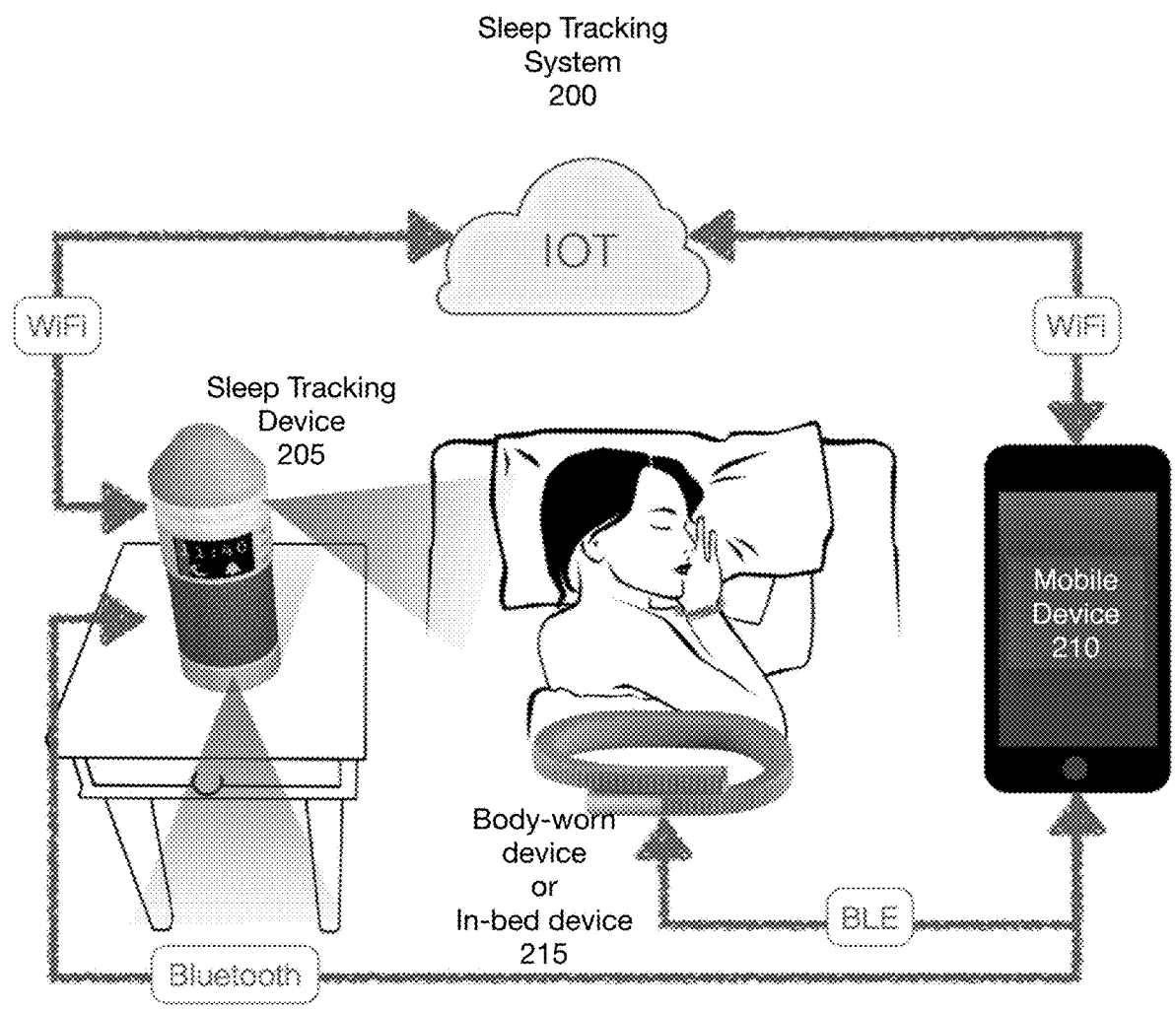
FIG. 2A is an exemplary diagram showing one embodiment of a sleep tracking system.

FIG. 2A is an exemplary diagram showing one embodiment of a sleep tracking system, including a sleep tracking device 205, a body-worn or in-bed device 215, and a mobile device 210. The sleep tracking system interacts via network connections. In one embodiment, the mobile device 210 and the sleep tracking device 205 interact via wireless connection (WiFi) or a Bluetooth connection. while the mobile device interacts with the body-worn device or in-bed device 215, via a low power Bluetooth connection (BLE), or another type of connection. The body-worn device or in-bed device 215 may interact with the sleep tracking device 205 via BLE or Bluetooth connection as well.

This system 200 works together to provide information about the user's sleep state, and to control the user's sleep environment. As noted above, the system need not include the body-worn device/in-bed device 215 or mobile device 210, but when such devices are available, the system may automatically connect to them and utilize the data available from them.

In one embodiment, the sleep tracking system may additionally include a wristband or similar body-worn device including one or more sensors. These sensors may be used to track the user's movements directly, using an accelerometer, gyroscope, or similar sensor. In one embodiment, the body-worn device may include sensors such as thermometers, to enable measurement of the user's body temperature. This can be useful for example, if the body-worn sensor detects that a user is experiencing a hot flash, the sleep tracking system can reduce the temperature of the room or the sleeping surface to improve the user's sleep cycle, keeping the user from waking up from the hot flash. In one embodiment, the sleep tracking system may control the body-worn device, to turn it, and or a subset of its sensors, on and off as needed. This reduces power use, since the body-worn device is battery dependent, but provides the additional sensor data when appropriate.

The sleep tracking system with the combined body-worn device 215 and table top sleep tracking device 205 may include a variety of functions and monitoring features that enable the monitoring and tracking of the user's activity. In one embodiment, the body-worn device 215 and/or mobile device 210 can track movements of the user during the day for a variety of purposes, such as calorie tracking. The body-worn device 215 or mobile device 210 can monitor the user's pulse, breathing rates, oxygen content, temperature, location, speed, etc. Thus, such devices can be used for medical purposes, such as reporting suspect conditions. Further, such devices can be used for exercise or physical fitness purposes, such as monitoring intensity of workouts, calories burned, heart rates, etc. Such devices may also be used to track to the location of individuals, such as a wondering child, employees of a service or repair company, etc. Thus, a single body-worn device that may include multiple such functions may easily find a need for 24-7 usage thereby greatly limiting the down time for charging. Therefore, shutting off the body-worn device when it is not needed, extends the time between charging. In one embodiment, the sleep tracking system may include a docking station to receive the body-worn device 215 and/or mobile device 210, and allow the device to operate on a bedside table at night while being plugged in for charging. This allows the device(s) to be continually used.

Any monitoring, body, sleep, sensor, band and communication, technology known to one of ordinary skill in the art, now or in the future, can be used in the sleep tracking system. The entire specifications from U.S. Pat. Nos. 7,647,195, 8,187,182 and 8,568,310 and U.S. application Ser. No. 13/622,325, filed on Sep. 18, 2012, U.S. Provisional Application No. 61/536,532, filed on Sep. 19, 2011, U.S. application Ser. No. 14/255,923, filed on Apr. 17, 2014, U.S. Provisional Application No. 61/814,178, filed on Apr. 19, 2013, U.S. application Ser. No. 14/269,036, filed May 2, 2014, which include, among other things, various sensor, body, band, controlled sleep surface technologies, are hereby incorporated by reference in their entirety herein.

Figure 2B:
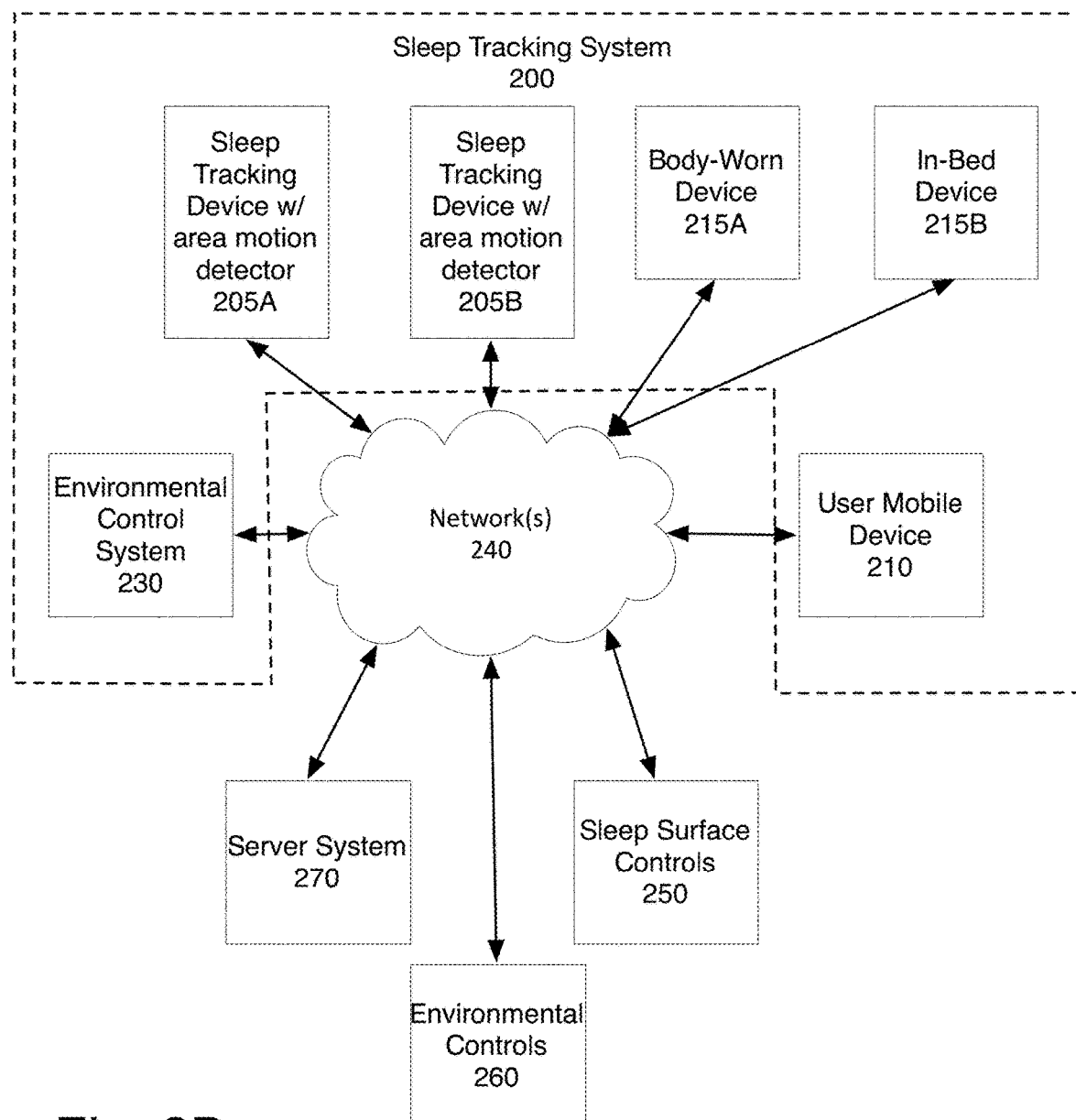
FIG. 2B is a system diagram showing interactions between a one embodiment of plurality of elements in a sleep tracking system.

FIG. 2B is a system diagram showing one embodiment of the interactions between a plurality of elements in a sleep tracking system. The sleep tracking system 200 includes one or more sleep tracking devices, with area motion detectors 205A, 205B. In one embodiment, the system further includes a body-worn device 215A, and/or in-bed device 215B. In one embodiment, the sleep tracking system 200 further includes a user mobile device 210. The user mobile device 210 may be a smart phone or similar device, in one embodiment including a sleep tracking or motion tracking application. In one embodiment, the user mobile device 210 may be used to control the sleep tracking device 205A, 205B, and provide more detailed output regarding the user's sleep quality and environment details, as well as enable the user to manually control the system and set preferences. In one embodiment, the user may also obtain detailed information about his or her sleep experience, and/or set preferences, via a webpage hosted on the server system 270, accessible through mobile device 210 or another computing device. In one embodiment, the sleep tracking devices may also include user interface elements, including optionally a touch screen, a browser, etc.

In one embodiment, the server system 270 receives data, via network 240 from sleep tracking device 205A, 205B, or user mobile device 210.

In one embodiment, the sleep tracking system 200 further includes environment control system 230. The environment control system 230 controls one or more environmental elements, such as a sleep control surface 250, or an environmental control 260, such as an air conditioning system or heating system, curtains, lights, air filter, or other environmental elements, which may be controlled via the sleep tracking system 200. Environmental control system 230 may also control other home automation elements, such as door locks, lights outside the sleeping area, a coffee machine in the kitchen, etc. The sleep tracking system 200, in one embodiment, can control any relevant controls in the house which are available for control.

The sensors may be in a single sleep tracking device, and thus at the same location or in multiple devices at different locations. Additionally, the sleep tracking system may include using more than one sleep tracking device with multiple sensors that either act independently or work together. In one embodiment, two sleep tracking devices are provided, and each monitors one or more users in the room. The devices communicate with each other to determine both the ideal environmental and sleep parameters for the individual user and the ideal environmental and sleep parameters for both the users combined. The sleep tracking devices, and optionally other devices when available, together form the sleep tracking system. Based on data from a plurality of sensors, the sleep tracking system logically determines the sleep phase of the user and adjusts the sleeping environment accordingly. The sleep tracking system 200 may also control various elements of the sleep tracking system itself. For example, when the sleep tracking device detects that the user is sleeping, the sleep tracking system may place the user's body-worn device into sleep mode. As noted above, this may be a mode to monitor the user's sleep or a mode to shut of some or all of the body-worn device to reduce power consumption.

Figure 3:
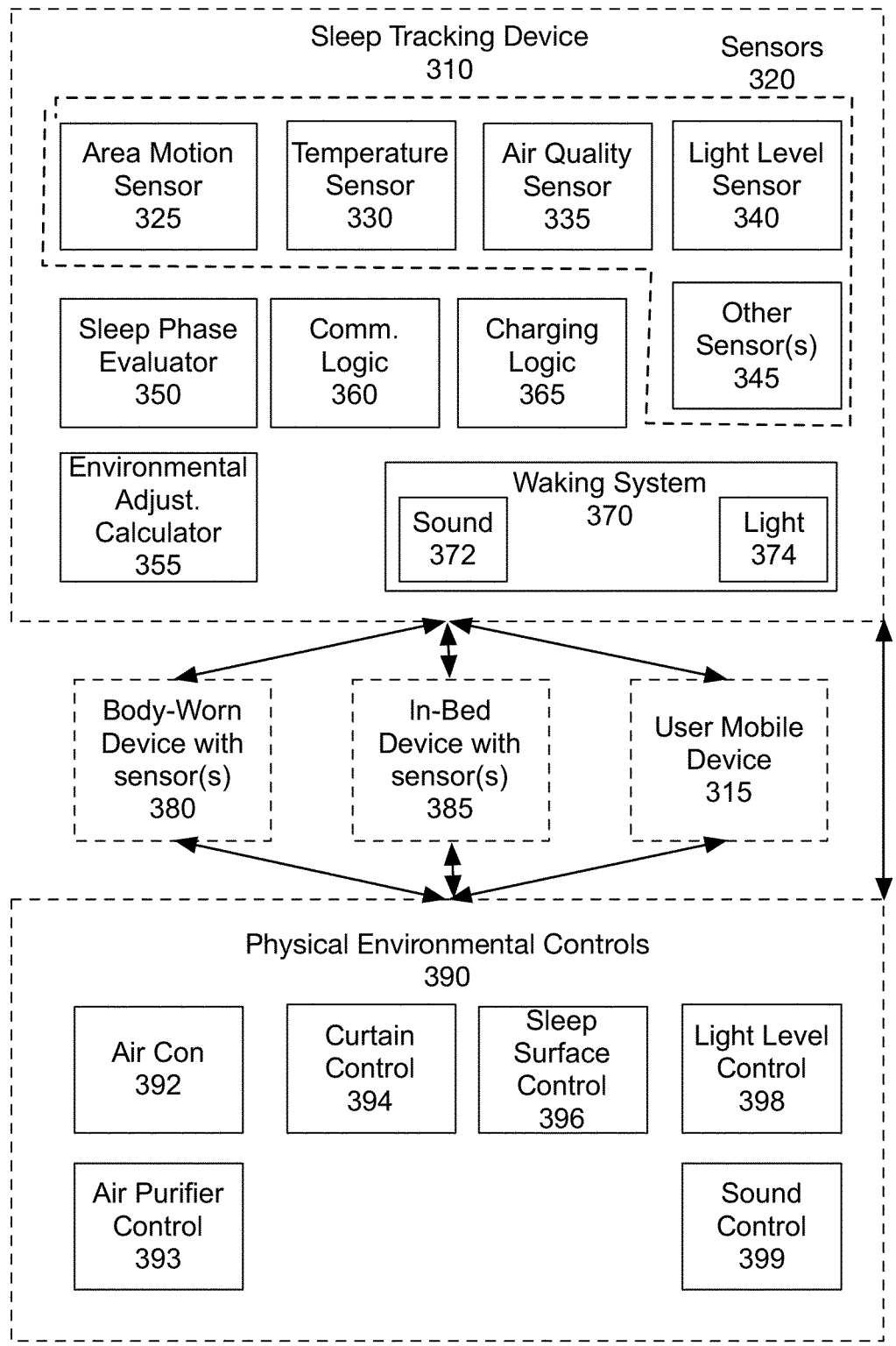
FIG. 3 is a block diagram showing aspects of at least one embodiment of the sleep tracking system.

FIG. 3 is a block diagram showing aspects of at least one embodiment of the sleep tracking system. The sleep tracking system can include one or more of a sleep tracking device 310, a user mobile device 315, a body-worn device with sensor(s) 380, and an in-bed device with sensor(s) 385. For simplicity, sensors are only shown in the sleep tracking device 310, though one of skill in the art would understand that a subset or superset of sensors may be present in the body-worn device 380, in-bed device 385, and/or user mobile device 315.

The sensors may include, for example, an area motion sensor 325, temperature sensor 330, air quality sensor 335, light level sensor 340, and other sensors 345. In one embodiment, the body-worn device 380 and/or in-bed device 385 may include an accelerometer or gyroscope to measure the user's movements. In one embodiment, the body-worn device 380 and/or in-bed device 385 may include a temperature sensor, to sense the user's body temperature. In one embodiment, the temperature sensor 330 may measure the user's body temperature as well as the room temperature.

In one embodiment, the air quality sensor 335 enables the sleep tracking system 310, in one embodiment, to monitor the user's bedroom's air quality to alert the user of unhealthy conditions and monitor correlations with sleep quality.

In one embodiment, the sleep phase evaluator 350 determines the user's sleep phase, based on the data from the sensors. Environmental adjustment calculator 355 utilizes the data from the sleep phase evaluator 350 and sensors 320, to determine whether the system should adjust the user's environment. The environment may include physical environmental controls 390, and waking system 370. The system uses communication logic 360 to control the physical environmental controls 390.

In one embodiment, the sleep tracking device 310 includes a charging logic 365, enabling a user to charge a mobile device, an in-bed device, and/or a body-worn device using the sleep tracking device 310 on the user's nightstand. The charging logic 365 can be used for charging an activity monitor that is normally worn by the user while awake and used to track various parameters of the user. The charging unit may be any of a variety of charging types, including smart chargers, etc., that can detect the charge currently on the battery and initiate an optimum charging sequence for the type of battery, if detectable and to ensure that the battery is charged but not overcharged or otherwise damaged. For instance, the embodiment can detect when a wearable activity monitor is connected and then examine the current charge on the battery of the wearable activity monitor. If the battery has an ID, the charger can read the type of battery information as well. The charger can then initiate a charging sequence to increase the charge on the battery in an optimum manner. In one embodiment, the charger may be a wireless charger that enables the device(s) to be charged through the air, without plugging in.

In one embodiment, the sleep tracking system may include a body-worn device, such as a wristwatch or bracelet styled device. Such embodiments may include an internal charger and an interface for receiving an external power source. Such embodiments may thus be worn by a user while awake and while sleeping or, may be removed during sleeping and plugged into a power source for charging. In the latter mode, the device can still monitor the user's sleep while sitting on a bedside table for charging.

In one embodiment, the sleep tracking device may include a docking station for a mobile device 315, an in-bed device 385, and/or a body-worn device 380. In such embodiments, the docking station may receive the device(s) and once coupled together, operate as a charging station for the device. For example, the mobile device 315, an in-bed device 385, and/or a body-worn device 380 may include sensors to detect motion, such as accelerometers, as well as any of the previously mentioned detection and tracking capabilities. When the user is going to sleep, the device can be connected to the docking station for charging. The sleep tracking device including the docking station can then use its own hardware and/or software, the hardware and/or software of the device or, a combination of both, to track the user's sleep while the device is charged.

Waking system 370 controls sound 372 and light 374, in one embodiment, provided by sleep tracking device 310. In one embodiment, the system adjusts the lighting and sound to help the user fall asleep, stay in the right sleep state, and wake up. The waking system 370 may include other elements, such as vibration or scents, in one embodiment. In one embodiment, other environmental controls may also be controlled by the waking system 370. For example, in one embodiment, the waking system 370 may start the user's coffee machine, when the user is starting to wake, to trigger the coffee smell as well as to provide fresh coffee to the user when he or she gets up.

The sensor signals may be used to continually monitor the user's sleep state and, when it is determined from the signals that the user has entered a stage of light sleep, the alarm time may be compared with the timing of the light stage of sleep (the "timing" of the sleep stage being a beginning time, an ending time and the period of time defined between). If the alarm time coincides with the timing of the entered stage of light sleep, an alarm or stimulus can be triggered to wake the user. The stimulus could be any of a variety of actions such as audible alarm, music, vibration, light, temperature fluctuations, other sounds, etc. In some embodiments, a gradually intensifying stimulus of light can be made to simulate a dawn event of the sun rising, gradually increasing noise, gradually decreasing white noise, etc..

In one embodiment, the light 374 is a smart reading light, which utilizes the information about when the user is falling asleep and initiates a lighting sequence that helps the user fall asleep faster when they choose to. Similarly, the sound 372 may select appropriate music and/or sound selections to create a calming and relaxed ambience for falling asleep faster. The light 374 and sound 372, and other environmental controls 390 may also be used to ensure that the user stays in the optimal sleep phase.

In one embodiment, the system turns off the light 374, when it determines the user is starting to fall asleep. In one embodiment, the sleep tracking device 310 may also provide a night light, which is available when the system determines the user has woken, and is likely to get out of bed, for example to go to the bathroom. In one embodiment, the light 374 also provides a reading light, which automatically turns off when the user falls asleep.

In one embodiment, the light 374 also may be used to guide the user to wakefulness, using a dawn-type lighting progression. In one embodiment, the light 374 may be a multi-color light, and the color tones may be selected to assist in waking and/or falling asleep. For example, the human body and brains is adapted to recognize the colors associated with the sun rising with wakefulness. Similarly, a user falls asleep more easily having been exposed to blue-toned lights rather than yellow toned lights, before falling asleep. Therefore, the light 374 may set the colors of the light to assist in the user's sleep and waking states.

In one embodiment, the speakers, lights or other sound or light emitting components of the sleep tracker device are arranged vertically to give the user the illusion or sensation of sound and/or light moving up and or around the room (e.g. waking up to the sun rising or noises that seem to get closer and/or farther from the user that gradually increase in volume).

In one embodiment, the user can set an alarm time, representing a desired time to wake up, in a personal device such as the user mobile device 315. In one embodiment, the system uses a master sleep cycle curve that is updated with data collected from the monitored signals and then analyzed to predict an upcoming stage of light sleep that the user may enter. Subsequently, an alarm time is compared to the predicted timing of the upcoming stage of light sleep and, if the alarm time coincides with the timing of the upcoming stage of light sleep, a start time is calculated for triggering an alarm to awaken the user. At the start time, an alarm comprising stimulus to awaken the user coincidentally with his entering the upcoming stage of light sleep.

In one embodiment, in addition to a user input alarm time, the sleep tracking system may synchronize with the users calendar in a the user's smart phone 315, on the cloud or otherwise accessible, and include information about the user, such as location, commute to meeting, desired leisure time, preparation time, etc., and then heuristically derive an optimal awakening time or window that would allow time for the user to accomplish the user's schedule. The alarm time represents a desired time that the user wishes to wake up, and is adjusted to a time when the system should start rousing the user, so that the user can be sure to be awake at the alarm time.

Other physical systems may optionally be controllable by sleep tracking system, either via sleep tracking device 310 or user mobile device 315. The physical environmental controls may include air conditioning 393, curtain controls to open and close curtains 394, sleep surface control 396 to alter the temperature and/or firmness of the sleeping surface, light level control 398 to alter the light level in the room (turn off, dim or brighten the light in the room), air purifier control 393, and sound control 399 to control external speakers and/or radio/music/sound players. Additionally, the sleep tracking system 310 may interface with any other device that can be controlled over a network, such as a door lock, coffee maker, teapot, remote start for a vehicle, etc.

Figure 4:
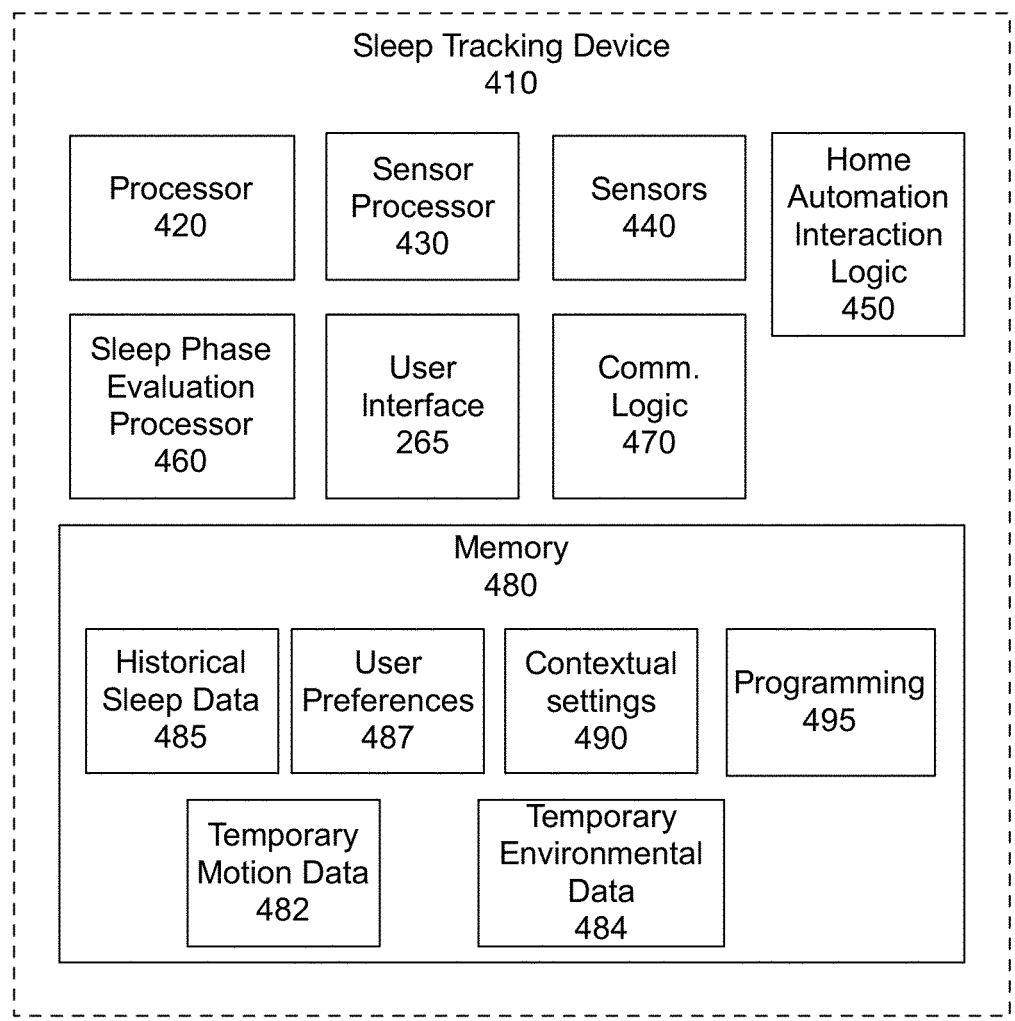
FIG. 4 is a block diagram showing aspects of at least one embodiment of the sleep tracking system.

FIG. 4 is a block diagram showing aspects of at least one embodiment of the sleep tracking system. The sleep tracking device 410 includes in one embodiment, a primary processor 420, a sensor processor 430, and a sleep phase evaluation processor 460. In another embodiment, device may include a single processor, more or fewer processors. The processors 420, 430, 460 may be a central processing unit (CPU), a digital signal processor (DSP), or another type of processing system. The sensors 440 in one embodiment may include the area motion sensor, temperature sensor, and other sensors. The system also may include communication logic 470, which in one embodiment, enables the sleep tracking device 410 to communication with outside systems. The system further includes a user interface 265 which enables the user to interact with the sleep tracking device 410. In one embodiment, the user interface 265 may be as simple as an alarm clock or light switch. In one embodiment, the user interface 265 may be as complex as keyboard or touch screen and LCD to receive input and/or provide output to the user.

In one embodiment, the memory 480 stores temporary motion data 482 and temporary environmental data 484, to enable the processors to use the data in predicting and analyzing the data.

In one embodiment, memory 480 includes historical sleep data 485, user preferences 487, programming 495, and contextual settings 490. Contextual settings 490 are the preferred settings for the user, based on the historical data and user preferences. In one embodiment, memory 480 may be a flash memory, or another type of non-volatile memory. Other forms of data storage, including ROM (read-only memory) may be used. In one embodiment, the programming, as well as contextual settings 490 may be updated from a server system (not shown). In one embodiment, the historical sleep data 485 may also be shared with the server system.

Figure 5:
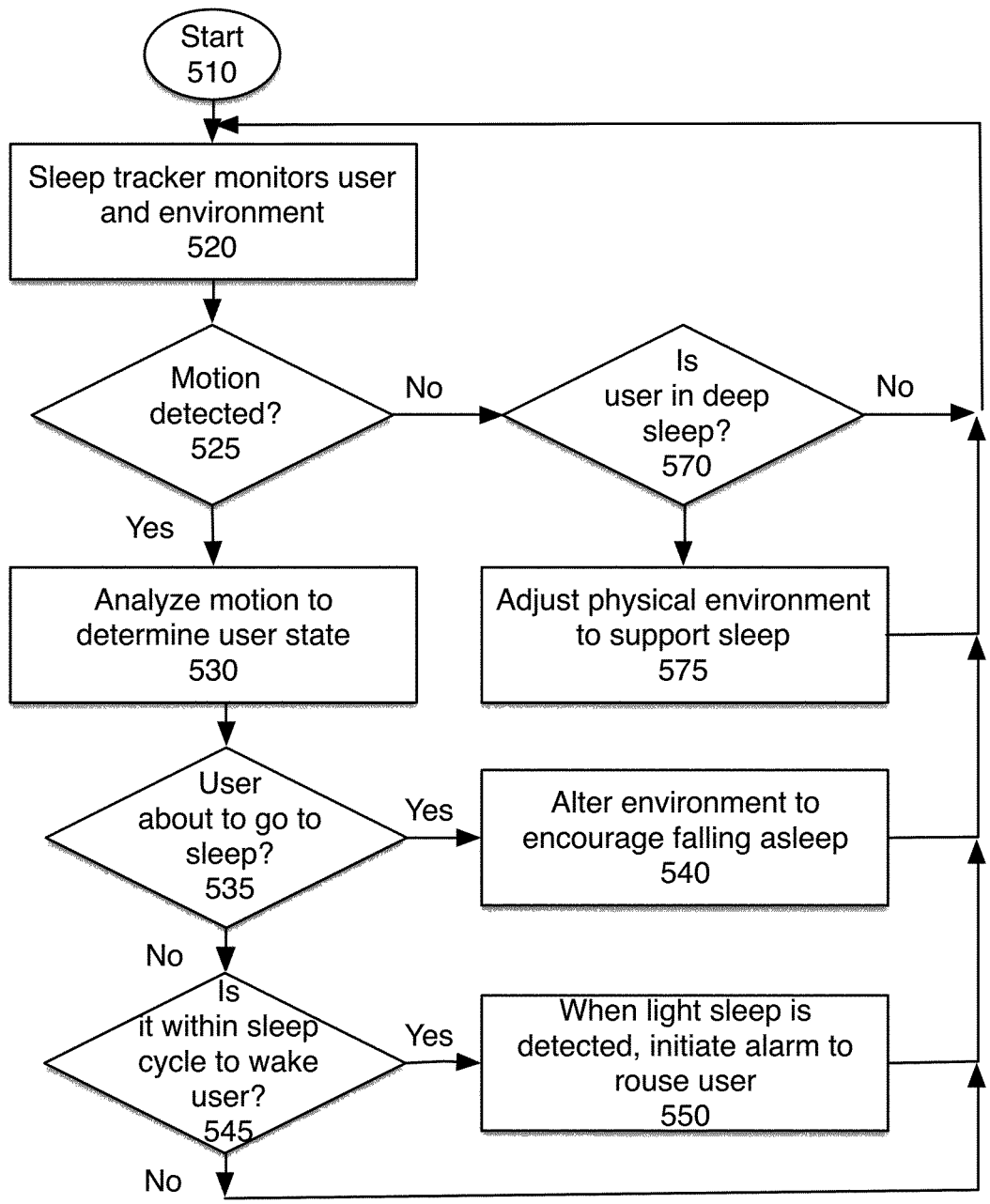
FIG. 5 is a flowchart of one embodiment of using the sleep tracking system.

FIG. 5 is a flowchart of one embodiment of using the sleep tracking system. The process starts at block 510. The process, at block 520, monitors the user and the user's environment.

At block 525, the process determines whether user motion was detected. If no motion was detected, the process determines whether the user is in deep sleep, at block 570. As noted, this determination may be made based on context and prior motion data. If the user is in deep sleep, at block 575, the physical environment is adjusted, if useful, to support sleep. The process then returns to block 520, to continue monitoring the user and his or her environment.

If the user is not in deep sleep, the process returns to block 520 to continue monitoring the environment and the user.

If motion was detected, at block 525, the process continues to block 530. At block 530, the motion is analyzed to determine the user state.

At block 535, the process determines whether the user is about to go to sleep. If so, at block 540, the user's environment is adjusted to encourage falling asleep. In one embodiment, the lights are turned off and music is played, if the user preferences indicate that this is OK. In one embodiment, other elements may also be controlled. For example, the temperature may be turned down, the curtains may be closed, etc. The process then returns to block 520 to continue monitoring.

If the user is not about to go to sleep, the process determines, at block 545, whether the user needs to be woken at the next light sleep cycle. If so, when light sleep is detected, the alarm is initiated to rouse the user. In one embodiment, the alarm utilized a gradual light and sound, to smoothly transition the user to wakefulness. As noted above, in one embodiment, the light may use the color tones and increasing intensity associated with the dawn. The process then returns to block 520, to continue monitoring the user and his or her environment. In one embodiment, this monitoring is continuous, whether or not the user is present. Because the system uses an area motion sensor, very little power is consumed in continuous monitoring.

One of ordinary skill in the art will recognize that the process is a conceptual representation of the operations used to monitor the user's sleep. The specific operations of the process may not be performed in the exact order shown and described. The specific operations may not be performed in one continuous series of operations, and different specific operations may be performed in different embodiments. Furthermore, the process could be implemented using several sub-processes, or as part of a larger macro process.

Figure 6:
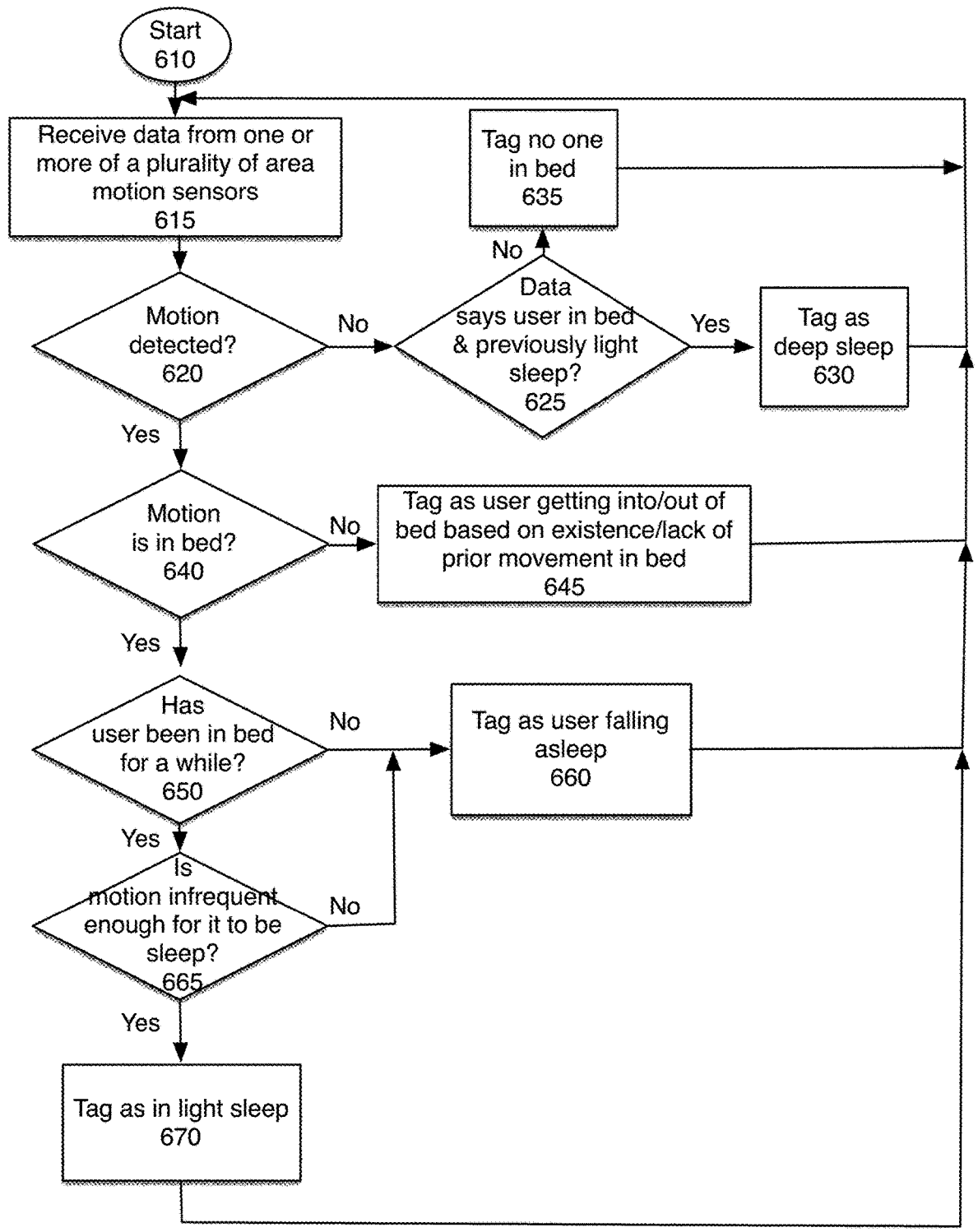
FIG. 6 is a flowchart of one embodiment of converting the digital data of an area sensor to determine sleep phases.

FIG. 6 is a flowchart of one embodiment of converting the digital data of an area sensor to determine sleep phases. The process starts at block 610. At block 615, the system receives data from one or more of a plurality of area sensors.

In one embodiment, as shown in FIG. 1A, the sleep tracking device comprises three area sensors A, B and C. Each sensor has a range in which the sensor would be triggered, illustrated as beams A, B, and C. Each motion sensor detects at least two different states (i.e., one state for movement and one state for non-movement). Three motion sensors with two states each can provide eight different logical combinations. Furthermore, the timing between the sensors being triggered adds additional information.

Table 1 below is an exemplary illustration of the eight logical combinations available with three digital area motion sensors:

TABLE 1

| Sensor Status | Predicted User State |
|---|---|
| A = on<br>B = off<br>C = off | User 2 Active Sleep cycle |
| A = on<br>B = on<br>C = off | User 1 Active Sleep cycle |
| A = on<br>B = off<br>C = on | User 2 Active sleep cycle,<br>User 1 entering bed |
| A = on<br>B = on<br>C = on | User getting into or out of bed |
| A = off<br>B = on<br>C = off | User 1 active sleep cycle |
| A = off<br>B = off<br>C = off | Deep sleep or empty bed |
| A = off<br>B = off<br>C = on | User is near bed |
| A = off<br>B = on<br>C = on | User sitting on side of bed/entering or exiting bed |

Based on the Table 1 above, if motion sensor A detected a movement while motion sensors B and C did not, it is likely that User 2 of FIG. 1 is moving but not User 1. On the other hand, if motion sensor C detected a movement while motion sensors A and B did not, it is likely User 1 is leaving or approaching the bed.

In one embodiment, the available data for a sleep monitoring device that includes two area motion sensors instead of three as shown in FIG. 1B is illustrated in Table 2.

TABLE 2

| A = on<br>B = off | User Active Sleep cycle |
|---|---|
| A = on<br>B = on | User getting into or out of bed |
| A = off<br>B = on | User is near bed |
| A = off<br>B = off | Deep sleep or empty bed |

Returning to FIG. 6, at block 620, the system determines whether motion was detected. If no motion was detected, the system determines, at block 625, whether the user is in bed, and thus in deep sleep, or not in bed.

In one embodiment, in addition to the actual sensing, the timing of the sensor activations is also useful for determining the actual current state. For example, if initially the signal indicates that the user is near the bed (A off, B off, C on), and then that the user is getting into bed (A on, B on, C on), and then that the user is active in bed (A on, B on, C off), the system can identify the sequence and determine what is occurring, e.g. that the user has gotten into bed and is getting ready to sleep.

If the system determines that the user has not entered the bed and gone through a light sleep stage, the system tags that no one is currently in bed. If the data says that the user has entered the bed, and gone through a light sleep stage, at block 630, the current user state is tagged as deep sleep.

If motion was detected, at block 620, the process continues to block 640. At block 640 the process determines whether the motion detected was in the bed. If not, the state is tagged as the user getting into or out of bed. In one embodiment, this is based on prior motion state, e.g. if previously there was motion in the bed, and now there is motion next to the bed, the system determines that the user is getting out of bed.

If the motion is in the bed, the process continues to block 650. At block 650, the process determines whether the user has been in bed for a while. If not, the system tags it as a user falling asleep, at block 660. If the user has not been in bed for a while, the process determines, at block 665, based on the frequency of motion, whether the user is asleep.

In addition, the duration between the times each sensor being triggered and/or the time in a day the sensor(s) being triggered may also be considered in determining the action of the user. For example, if motion sensors A and B and C detect a motion around 3-5 am in the morning, then detect no motion for the following 3 -5 minutes, and again detect motion after that, it is likely that User 1 temporarily left the bed (e.g., using restroom, drinking water, etc.). Similarly, if sensor C detects movement before sensor B, it is more likely that User 1 is getting onto the bed rather than getting off the bed.

If the motion is frequent enough, at block 670, the sleep state is tagged as light sleep. The process then returns to block 615, to continue receiving data.

Based on the logical information obtained from the response of the sensors, and the sequence of activations, the sleep tracking system determines the user's sleep state. This sleep state can be used to adjust the user's environment.

One of ordinary skill in the art will recognize that the process is a conceptual representation of the operations to convert the digital data of an area sensor to determine sleep phases. The specific operations of the process may not be performed in the exact order shown and described. The specific operations may not be performed in one continuous series of operations, and different specific operations may be performed in different embodiments. Furthermore, the process could be implemented using several sub-processes, or as part of a larger macro process.

Figure 7:
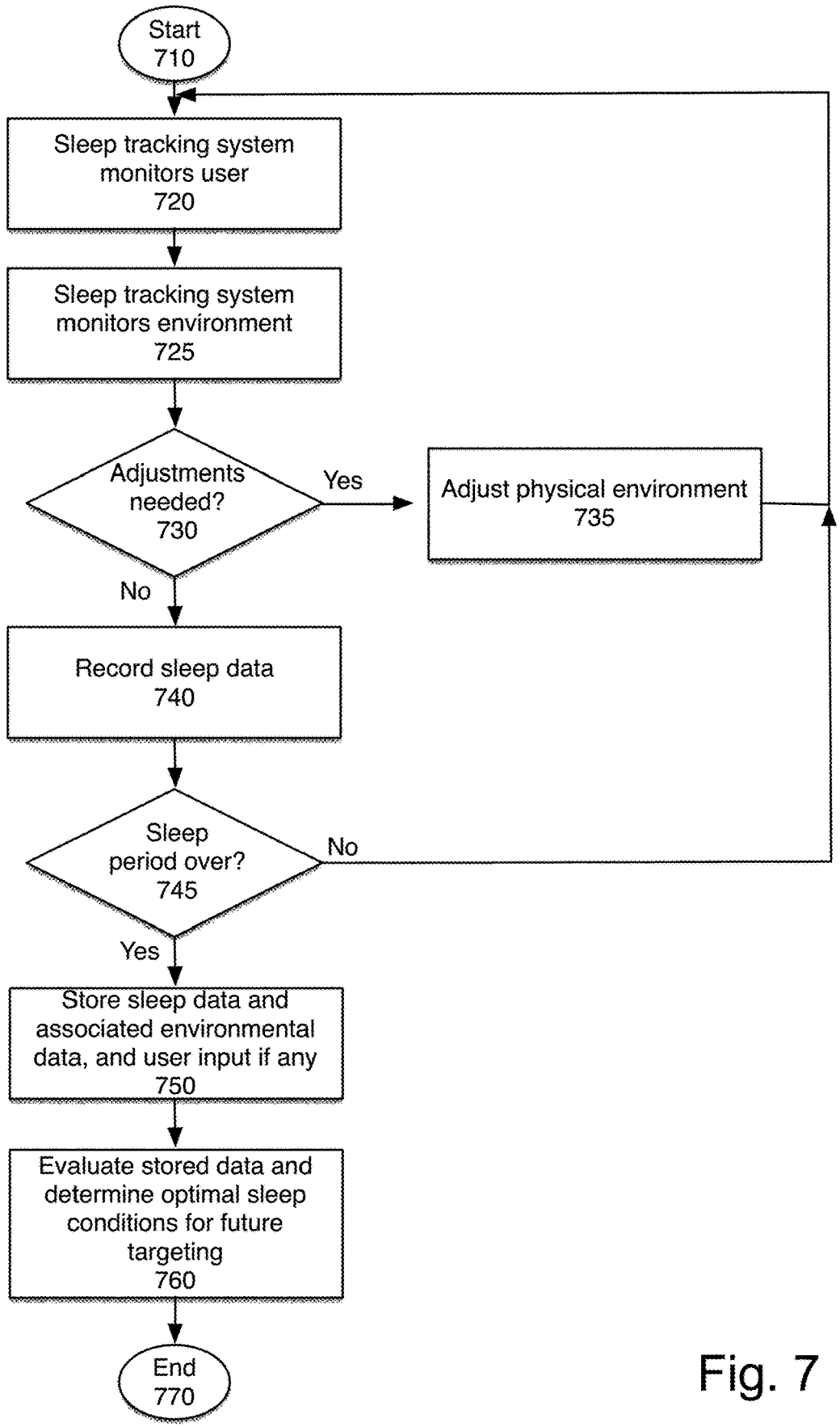
FIG. 7 is a flowchart of one embodiment of using the sleep tracking system to optimize the user's environment.

FIG. 7 is a flowchart of one embodiment of using the sleep tracking system to optimize the user's environment. The process starts at block 710. At block 720, the sleep tracking system monitors the user. At block 725, the sleep tracking system monitors the user's environment.

At block 730, the process determines whether any adjustments are needed. The sleep tracking system can take actions to maximize the user's sleep quality. For example, when the sensors detect that User 1 of FIG. 1A or 1B is approaching the bed around 11:30 pm and has not left the bed in the following few minutes, the sleep tracking device will conclude that User 1 is in the process of going to sleep. The sleep tracking device will turn the light off (either instantly or gradually) and/or start a pre-selected music or white noise to assist sleep. In one embodiment, the change in the pattern of movement from reading in bed, or going to sleep, and falling asleep is detected. Action initiated by the sleep tracking device can be customized based on the user's preferences.

Once the user is determined to have fallen asleep, the sleep tracking device may turn off the music and/or start lowering the temperature of the mattress or room to maximize the user's sleep quality.

In one embodiment, the sensors used by the sleep tracking system are not limited to area motion sensors. The sleep tracking system may further include be temperature sensors, light sensors (such as photodiodes), air quality sensors, etc. Thus, the sleep tracking device can also monitor environmental conditions, such as the temperature of the mattress, brightness of the room, and the quality of the air (e.g., carbon dioxide or oxygen levels). In one embodiment, the sleep tracking system may also be able to make adjustments to other local conditions and aspects of the user's home.

If no adjustments are needed, the sleep data is recorded, at block 740. At block 745, the process determines whether the sleep period is over. If not, the process returns to block 720 to continue monitoring the user.

If the sleep period is over, the sleep data is recorded. The sleep data recorded may include relevant environmental data, control information as well as local data.

In one embodiment, the user of the device can provide information regarding his or her activities, level of tiredness and/or sleep patterns, quality, or duration. This data is also recorded, at block 750. The device takes that information into consideration when determining the ideal conditions and environmental and sleep parameters for the user. For example, the user can indicate that he or she is more tired than usual. The sleep tracking device can take this information into consideration when determining the user's optimal sleep parameters.

At block 760, the system evaluates the stored data, and determines the optimal sleep conditions for future targeting. In one embodiment, the sleep tracking device monitors the user's sleep throughout the night and adjusts the user's environment to ensure that the user has an optimal sleep experience. In one embodiment, the adjustment may include adjusting the temperature of the sleeping surface or room. For example, if the sleep tracking device predicts that the user is about to get up and leave the bed (i.e., to use the restroom), the sleep tracking device may adjust the temperature of the room or mattress beforehand so that the user will not feel great discomfort when leaving the bed, which typically will allow the user to fall back sleep quicker afterwards and result in a better sleep.

One of ordinary skill in the art will recognize that the process is a conceptual representation of the operations to use the sleep tracking system to optimize the user's environment. The specific operations of the process may not be performed in the exact order shown and described. The specific operations may not be performed in one continuous series of operations, and different specific operations may be performed in different embodiments. Furthermore, the process could be implemented using several sub-processes, or as part of a larger macro process.

As used in this description, the terms "component," "database," "module," "system," "processing component" and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet or local Wi-Fi with other systems by way of the signal).

Aspects, features and advantages of several exemplary embodiments of the present disclosure will become better understood with regard to the following description in connection with the accompanying drawing(s). It should be apparent to those skilled in the art that the described embodiments of the present disclosure provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated and equivalents thereto. Hence, use of absolute terms such as, for example, "will," "will not," "shall," "shall not," "must" and "must not" are not meant to limit the scope of the present invention as the embodiments disclosed herein are merely exemplary.

In this description, the terms "phase," "sleep phase" and "sleep period" are used interchangeably to represent a block of time, from sleep entry to awakening, during which a person sleeps. The terms "stage," "sleep stage," "light stage" and "deep stage" are used to describe smaller spans of time within a larger "sleep period" that may combine in various combinations to form one or more "sleep cycles." As such, one of ordinary skill in the art will recognize that multiple "sleep stages" may be combined to form a "sleep cycle" and multiple "sleep cycles" may be combined to form a "sleep period."

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed. It should be appreciated that the present invention could be performed on a device such as a computer or any device having a processor and memory or on a computer readable medium to be used on or executed by a computer. The term "content" may also include files having executable content, such as: object code, scripts, byte code, markup language files, and patches. In addition, "content," as referred to herein, may also include files that are not executable in nature, such as documents that may need to be opened or other data files that need to be accessed.

What is claimed is:

1. A sleep tracking system to determine one or more users' sleep state comprising:
    an area motion detector including a first area motion sensor and a second area motion sensor to determine the sleep state of one or more users, the first area motion sensor and the second area motion sensor defining a plurality of non-overlapping zones on one bed, such that motion of each of the one or more users in any of the zones is detected by one of the first area motion sensor and the second area motion sensor, the first area motion sensor and the second area motion sensor being non-contact sensors; a third area motion sensor to detect motion of at least one of the one or more users getting out of the bed in a second zone next to the bed, the second zone including an area next to the bed that does not overlap with the bed, where the first area motion sensor, the second area motion sensor, and the third area motion sensor are in a single device; and
    a processor configured to use data from the first area motion sensor, the second area motion sensor, and the third area motion sensor to determine the one or more users' sleep state.

2. The sleep tracking system of claim 1, wherein the first and second area motion sensors in the area motion detector comprises one of: a passive infrared (PIR), a proximity sensor using one or more of radio waves, ultraviolet, and thermal mechanisms, microwave/radar sensor, area reflective sensor, and ultrasonic sensor.

3. The sleep tracking system of claim 1, wherein the first, second, and third area motion sensors provide a digital reading, the digital reading comprising one of "motion detected" and a "motion not detected" indication.

4. The sleep tracking system of claim 1, further comprising:
    a memory to store data from the first, second, and third area motion sensors; and
    the processor to use data from the memory as prior data, and the data from the first, second, and third area motion sensors as current data, the data from the memory providing context to enable determination of the user's current sleep state based on the prior data and the current data.

5. The sleep tracking system of claim 1, wherein the first, second, and third area motion sensors are used to identify motion for each of a plurality of users in the bed, such that the sleep state of each of the plurality of users is determined, the sleep state of one user being determined by at least two of the first, second, and third area motion sensors.

6. The sleep tracking system of claim 1, further comprising:
    an environmental control system interacting with one or more environmental controls external to the sleep tracking system, the environmental control system adjusting the environmental controls to optimize a sleep environment based on the user's sleep state.

7. The sleep tracking system of claim 1, wherein the sleep tracking system detects motion by two users in the one bed, to determine the sleep state of the two users.

8. The sleep tracking system of claim 7, further comprising:
    at least three sensors detecting motion by the two users, data from the at least three sensors used in determining the sleep state of the two users, the at least three sensors located in one, two, or three area motion detectors.

9. The sleep tracking system of claim 7, further comprising:
    an accelerometer-based movement detector detecting the movement of at least one of the two users, for determining the sleep state.

10. The sleep tracking system of claim 7, further comprising:
    an environmental control system interacting with one or more environmental controls external to the sleep tracking system, the environmental control system adjusting the environmental controls to optimize a sleep environment for the two users, based on both users' sleep state.

11. The sleep tracking system of claim 10, wherein at least one of the environmental controls is optimized for a particular user, the at least one environmental control selected from among: a temperature, a light level, sleep surface softness, and sounds, and the environmental control is calibrated to reduce impact on a second user.

12. A passive motion sensing sleep tracking system to determine one or more users' sleep state comprising:
    an area motion sensor to detect motion in a first zone on a bed, the area motion sensor selected from among: a passive infrared (PIR), a proximity sensor, microwave/radar sensor, area reflective sensor, and ultrasonic sensor, the area motion sensor having two states: ON indicating movement and OFF indicating no movement;

a second area motion sensor to detect motion in a second zone on the bed, the second area motion sensor having two states: ON indicating movement and OFF indicating no movement, wherein the first zone and the second zone do not overlap, wherein the area motion sensor defining the first zone and the second area motion sensor are in a single device; and a processor to use data from the first area motion sensor and the second area motion sensor to determine the sleep state of each of the one or more users.

13. The passive motion sensing sleep tracking system of claim 12, wherein the area motion sensor provides a digital reading, the digital reading comprising one of "motion detected" and a "motion not detected" indication.

14. The passive motion sensing sleep tracking system of claim 12, further comprising:
  a memory to store data from the area motion sensor; and
  the processor to use historical data from the memory in combination with current data from the area motion sensor, to determine of the user's current sleep state based on the historical data and the current data.

15. The passive motion sensing sleep tracking system of claim 12, further comprising:
  a plurality of area motion sensors, to monitor motion in a plurality of zones on a bed; and
  the processor to identify the sleep state of two users on the bed, based on the data from the plurality of area motion sensors.

16. A method of using an area motion sensing sleep tracking system for determining a sleep state for a plurality of users, the method comprising:
  receiving motion data from an area motion sensor defining a first zone on a single sleep surface, the area motion sensor selected from among: a passive infrared (PIR), a proximity sensor, microwave/radar sensor, area reflective sensor, and ultrasonic sensor, the area motion sensor being a non-contact sensor, in order to measure movement;
  receiving motion data from a second area motion sensor, the motion data associated with a second zone on the sleep surface, wherein the first zone and the second zone do not overlap;
  receiving motion data from a third area motion sensor to detect motion of one or more of the plurality of users getting out of the bed in a third zone next to the bed, the third zone including an area next to the bed that does not overlap with the bed, wherein the first zone, the second zone, and the third zone do not overlap and wherein the area motion sensor defining the first zone, the second area motion sensor, and the third area motion sensor are in a single device; and
  processing the motion data, from the area motion sensor, the second area motion sensor, and the third area motion sensor, and utilizing the motion data and historical motion data to determine the sleep state of the plurality of users.

17. The method of claim 16, wherein the motion data is a digital reading, the digital reading comprising one of "motion detected" and a "motion not detected."

18. The method of claim 16, further comprising:
  receiving motion data from a plurality of area motion sensors, each of the plurality of area motion sensors sensing motion in a zone on a bed; and
  determining the sleep state of two users on the bed,
  the processor to identify the sleep state of two users on the bed, based on the data from the plurality of area motion sensors.

19. The passive motion sensing sleep tracking system of claim 12, further comprising:
  a third area motion sensor to detect motion of at least one of the one or more users in a third zone next to the bed, wherein the third zone does not overlap the first zone and the second zone and wherein the third area motion sensor is in the single device.

* * * * *

UNITED STATES PATENT AND TRADEMARK OFFICE
CERTIFICATE OF CORRECTION

| | | |
|---|---|---|
| PATENT NO. | : 10,568,565 B1 | Page 1 of 1 |
| APPLICATION NO. | : 14/469509 | |
| DATED | : February 25, 2020 | |
| INVENTOR(S) | : Philippe Richard Kahn et al. | |

It is certified that error appears in the above-identified patent and that said Letters Patent is hereby corrected as shown below:

On the Title Page

The inventorship is updated as follows:
(72) Inventors: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US); Steven D. Powell, Provo, UT (US)

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*